United States Patent [19]

Yabe et al.

[11] Patent Number: 5,315,383
[45] Date of Patent: May 24, 1994

[54] ENDOSCOPE SYSTEM

[75] Inventors: Hisao Yabe; Hiroyuki Sasa; Shigeru Nakajima; Kazunari Nakamura; Yoshihiro Okada; Katsuyuki Saito; Seiji Yamaguchi, all of Tokyo, Japan

[73] Assignee: Olympus Optical Co., Ltd., Tokyo, Japan

[21] Appl. No.: 842,704

[22] Filed: Feb. 27, 1992

[51] Int. Cl.$^5$ ............................ A61B 1/04; A61B 1/06
[52] U.S. Cl. ............................................ 348/68; 348/72
[58] Field of Search ...................... 358/98; H04N 7/18

[56] References Cited

U.S. PATENT DOCUMENTS

| 4,774,568 | 9/1988 | Matsuo | 358/98 |
| 4,816,909 | 3/1989 | Kimura et al. | 358/98 |
| 4,853,773 | 8/1989 | Hibano | 358/98 |
| 4,855,819 | 8/1989 | Hibino et al. | 358/98 |
| 4,891,695 | 1/1990 | Uchikubo et al. | 358/98 |
| 4,926,258 | 5/1990 | Sasaki et al. | 358/98 |
| 4,967,269 | 10/1990 | Sasagawa | 358/98 |

FOREIGN PATENT DOCUMENTS 63-200736 8/1988 Japan .
63-220837 9/1988 Japan .
63-304221 12/1988 Japan .
2-305543 12/1990 Japan .

Primary Examiner—Howard W. Britton
Attorney, Agent, or Firm—Armstrong, Westerman, Hattori, McLeland & Naughton

[57] ABSTRACT

An endoscope system includes a plurality of different endoscopes each of which has an illumination optical system for emitting light outward, an observation optical system for forming an optical image of a subject at the distal end of an insertion tube which can be inserted into the subject, and a solid-state imaging device for converting the optical image of the subject formed by the observation optical system into an electric signal, a plurality of different signal processors each of which drives a solid-state imaging device and processes the output signal sent from the solid-state imaging device to provide a video signal, and a plurality of different light sources each of which is compatible with one of the plurality of different endoscopes and supplies light to the illumination optical system. The system expendability is so excellent that the above equipment will be compatible with technologically-upgraded endoscopes, signal processors, or light sources.

8 Claims, 12 Drawing Sheets

ENDOSCOPE SYSTEM

BACKGROUND OF THE INVENTION

1. Field of the Invention

The present invention relates to an endoscope system permitting expandable combinations of endoscopes, signal processors, and light sources.

2. Description of the Related Art

Endoscopes have been adopted widely in recent years, so that an elongated insertion tube can be inserted into a body cavity to observe organs in the cavity, or a treatment adapter can be routed through a treatment channel, if necessary, to perform various treatments. Endoscopes are used not only for medical but also industrial purposes; such as, observation or inspection of objects in pipes of boilers, machines, or chemical plants, or those in machines.

The aforesaid endoscope may be either an optical endoscope (so-called fiberscopes) permitting observation with naked eyes based on image fiber technologies, or an electronic endoscope having a solid-state imaging device at the tip of an insertion tube to observe subjects on a TV monitor.

An endoscope apparatus having an electronic endoscope requires not only a light source but also a signal processor for driving a solid-state imaging device, and for processing the output signal of the solid-state imaging device to generate a video signal. The endoscope apparatus provides high-resolution images and permits easy image recording and reproduction.

Therefore, electronic endoscopes have taken over from fiberscopes as a mainstream tool of endoscopy nowadays. The core of endoscopic technologies has shifted from image fiber technologies to electronic technologies. More specifically, a semiconducting technology relating to improvement of a charge coupled device (hereafter, CCD) or any other solid-state imaging device, an imaging circuit technology (video process technology) for driving the solid-state imaging device and converting the output signal into a video signal, and a light adjustment technology relating to a light source have become main targets that must be tackled in order to develop endoscope-related technologies.

Under these circumstances, an endoscope apparatus commercialized with state-of-the-art technologies at one point in time rapidly becomes a technologically obsolete because of rapid advancements in the fields of semiconducting, imaging circuitry, and light adjustment. Users who have purchased certain products may be disappointed at finding the debut of a new product or an upgraded version.

Only certain types of signal processors and light sources can usually be combined with certain models of endoscopes due to the differences in the number of pixels of solid-state imaging device and the driving mode, or the difference in color imaging; that is, field sequential or simultaneous (color mosaic) imaging. Even if new products are put on the market, they are nothing but improved versions of previous models. In order to utilize the improved part, users are required to purchase new endoscope apparatuses or keep using existing ones.

To cope with this problem, various proposals have been made to permit the use of the same equipment regardless of the difference in the type of solid-state imaging device or imaging mode. For example, U.S. Pat. Nos. 4,774,568, 4,816,909, 4,891,695, 4,926,258 all disclose endoscopes using different types of solid-state imaging devices. U.S. Pat. Nos. 4,853,773, 4,855,819, Japanese Patent Laid-Open No. 1988-200736, Japanese Patent Laid-Open No. 1988-220837, Japanese Patent Laid-Open No. 1988-304221, and Japanese Patent Laid-Open No. 1990-305543 all disclose related art capable of operating in different imaging modes.

U.S. Pat. No. 4,774,568 discloses an endoscope apparatus in which endoscopes operating the same imaging mode but having different types of solid-state imaging devices can be used. Therein, a connector for connecting between an endoscope and a main unit is provided with an ID detection member for identifying the imaging position of a solid-state imaging device incorporated in an endoscope, and the image format of a reflected image or unreflected image. Depending on the signal the ID detection member detects, it is determined whether the focal position of a solid-state imaging device is set to forward observation, lateral observation, or backward observation, or whether images are displayed laterally or reversely. Thus, formed images are displayed at a correct position on a TV monitor. In U.S. Pat. No. 4,816,909, an endoscope connector is provided with a ROM containing information indicating the number of pixels of a solid-state imaging device and the spectral characteristic for each endoscope. Then, depending on the information read from the ROM, either a drive or processing circuit is selected.

In U.S. Pat. No. 4,891,695, at least one pixel element of a solid-state imaging device in an endoscope is designed to that the area or at least one lateral side will be the same as that of an effective pixel. Thereby, a pixel configuration is detected to control a video signal processing means. U.S. Pat. No. 4,926,258 discloses an endoscope apparatus in which endoscopes having solid-state imaging devices provide different numbers of pixels. Therein, a drive signal containing a horizontal transfer clock with certain frequencies is applied to a solid-state imaging device and then the signal read from the solid-state imaging device is processed to generate a video signal.

On the other hand, U.S. Pat. No. 4,853,773 discloses an endoscope signal processing apparatus, supporting different imaging modes, wherein an endoscopic signal processing unit is equipped with a first signal processor for processing the signal sent from a field sequential type imaging device, and a second signal processor for processing the signal sent from a simultaneous type imaging device. The endoscopic signal processing unit identifies the imaging mode of an endoscope connected, selects a corresponding signal processor, then outputs a video signal. U.S. Pat. No. 4,855,819 discloses an endoscope imaging system in which a field sequential type light source and signal processor, and a simultaneous type light source and signal processor are accommodated in one housing. Connectors are formed for both imaging modes, so that either field sequential type or simultaneous type endoscopes can be used.

Japanese patent Laid-Open No. 1988-20736 discloses an endoscope imaging apparatus in which a common circuit is used as parts of a signal processor for field sequential type color imaging system endoscopes and a signal processor for color mosaic imaging system endoscopes. In Japanese Patent Laid-Open No. 1988-220837, a signal processor for field sequential type color imaging system endoscopes and a signal processor for color mosaic imaging system endoscopes are mutually connectable, so that one of the panels can be used to adjust the gain of the other signal processor.

Moreover, Japanese Patent Laid-Open No. 1988-304221 discloses an endoscope apparatus in which an external TV camera of an endoscope whose image transmission optical system has a final image forming position outside of the main unit is provided with a type signal generation circuit for generating an identification type signal. Depending on the identification type signal sent from the type signal generation circuit, simultaneous or field sequential imaging is determined to select an associated light source and signal processor. Japanese Patent Laid-Open No. 1990-305543 discloses an endoscope in which a user presses a switch to specify whether to adopt simultaneous or field sequential imaging, then a mosaic filter or a light transmission body is arranged by an electrostatic motor on a photosensitive section of a solid-state imaging device depending on the simultaneous or field sequential imaging mode. Then, the identification signal sent from the type signal generation circuit is checked to determine either the simultaneous or field sequential imaging mode, then an associated light source and signal processor are selected.

However, when a means for identifying the type of endoscope is installed, or light sources or signal processors of field sequential and simultaneous imaging modes are prepared, the product becomes so expensive that users have to incur an enormous amount of equipment investment. Besides, the endoscope apparatus becomes very large and heavy.

Even if functions are installed in a single unit or system to cope with different types of endoscopes, all of the functions are not used for normal operation and many functions remain idle. This opposes the concept of effective use of equipment and wastes equipment.

A unit or a function of a system a user is currently using and dissatisfied with differs from user to user. For example, a user may be disappointed with insufficient resolution of endoscopic images, but another user may be annoyed with slow light adjustment or color aberration.

Even if a single unit or system is upgraded, partial improvements in semiconducting technologies relating to improvement of a solid-state imaging device, imaging circuit technologies, or light source light adjustment technologies are not implemented in the unit or system according to needs from users.

SUMMARY OF THE INVENTION

An object of the present invention is to provide an evolvable endoscope system in which an existing light source can be used in combination with new endoscopes integrating advanced endoscopic technologies.

Another object of the invention is to provide an evolvable endoscope system in which an existing endoscope can be used in combination with new light sources integrating an advanced light source technology.

Another object of the invention is to provide an evolvable endoscope system in which an existing endoscope can be used in combination with new signal processors integrating an advanced signal processing technology.

Another object of the invention is to provide an evolvable endoscope system in which an existing light source can be used in combination with new signal processors integrating an advanced signal processing technology.

Another object of the invention is to provide an endoscope system allowing users to operate endoscope apparatuses integrating state-of-the-art technologies with limited investment in equipment.

Another object of the invention is to provide an endoscope system for realizing upgraded components with limited equipment investment according to the needs of a user.

In order to achieve these and other objects, an endoscope system according to the present invention includes a plurality of different endoscopes, each of which has an illumination optical system for emitting light outward, an observation optical system for forming an optical image of a subject at the distal end of an insertion tube that can be inserted into the subject, and a solid-state imaging device for converting the optical image of the subject formed by the observation optical system into an electric signal, a plurality of signal processors for driving the solid-state imaging device, and for processing the output signal of the solid-state imaging device to provide a video signal, and a plurality of different light sources which are compatible with any of the plurality of different endoscopes and supply light to illumination optical system. One of the plurality of different endoscopes is connected to a compatible one of the plurality of different signal processors and any one of the plurality of different light sources, thus forming an endoscope apparatus.

Other features and advantages of the present invention will be apparent in conjunction with the description below.

BRIEF DESCRIPTION OF THE DRAWINGS

FIG. 1 is an explanatory diagram showing the connecting relationships in an endoscope system;

FIG. 2 is a specific configuration diagram of an endoscope apparatus including a first endoscope, a first video processor, and a first light source;

FIG. 3 is a specific configuration diagram of an endoscope apparatus including the first endoscope and first video processor, and a second light source;

FIG. 4 is a specific configuration diagram of an endoscope apparatus including the second endoscope, second video processor, and first light source;

FIG. 5 is a specific configuration diagram of an endoscope apparatus including the second endoscope, second video processor, and second light source;

FIG. 7 is an explanatory diagram showing the connecting relationships in an endoscope system;

FIG. 8 is a specific configuration diagram of an endoscope apparatus including a first endoscope, a first video processor, and a first light source;

FIG. 9 is a specific configuration diagram of an endoscope apparatus including a second endoscope, a second video processor, and a second light source;

FIG. 11 is a specific configuration diagram of an endoscope apparatus including a first endoscope, a first video processor, and a first light source; and FIG. 12 is a specific configuration diagram of an endoscope apparatus including a second endoscope, a second video processor, and a second light source.

DETAILED DESCRIPTION OF THE PREFERRED EMBODIMENTS

FIGS. 1 to 5 show the first embodiment of the present invention.

Figure 1:
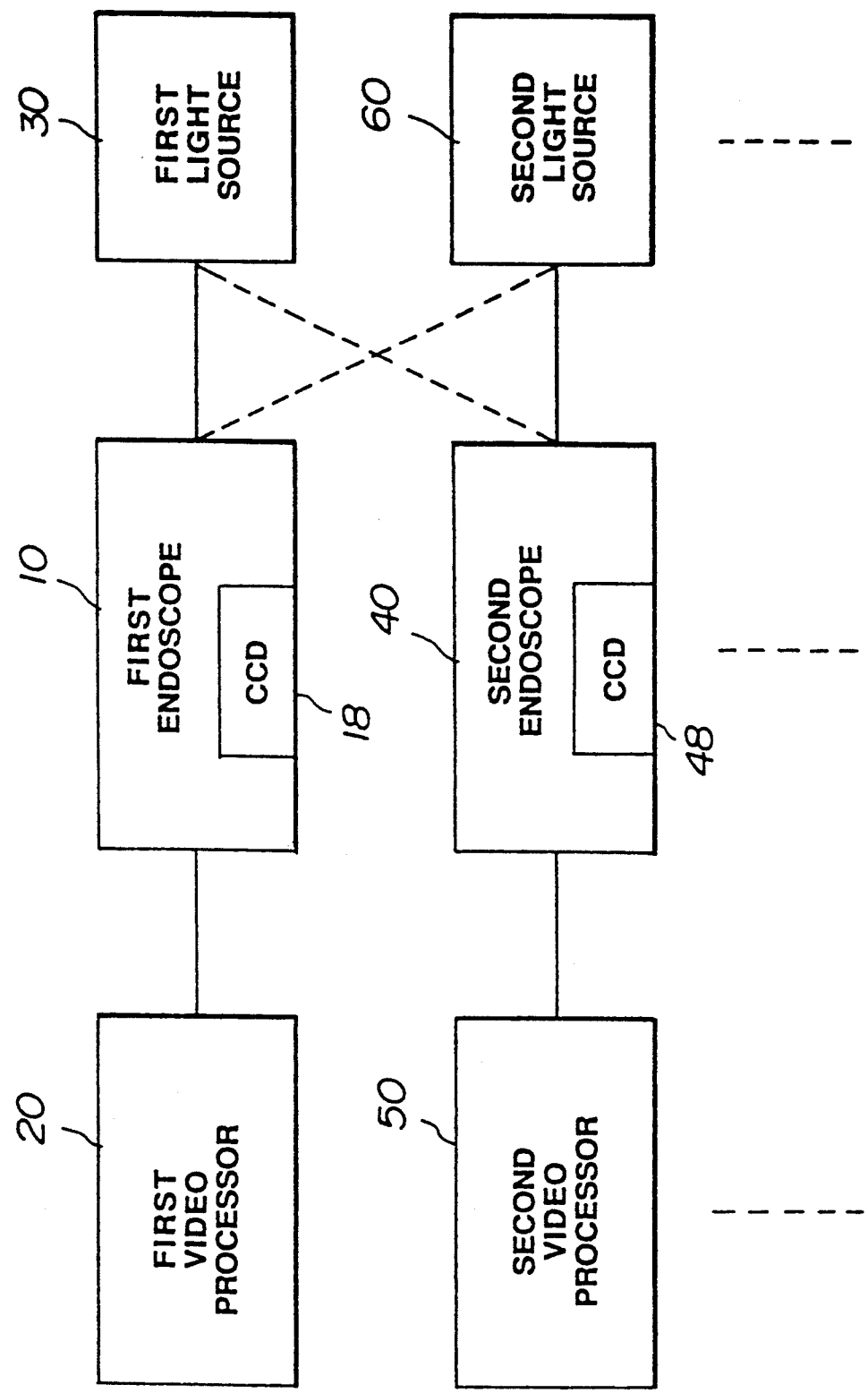
FIGS. 1 to 5 show the first embodiment of the present invention.

As shown in FIG. 1, an endoscope system of this embodiment includes a first endoscope 10 equipped with a CCD 18 as a solid-state imaging device, a first video processor 20 or a signal processor for driving the CCD 18 in the first endoscope 10 and processing signals sent from the CCD 18, a first light source 30 for supplying illumination light, a second endoscope 40 equipped with a CCD 48, a second video processor 50 or a signal processor for driving the CCD 48 in the second endoscope 40 and processing signals sent from the CCD 48, and a second light source 60 for supplying illumination light, as well as third, fourth, etc. endoscopes, third, fourth, etc. video processors, and third, fourth, etc. light sources, which are not shown.

In endoscope systems of this and subsequent embodiments, specific examples will be described in conjunction with two endoscopes, two video processors, and two or one light sources.

The first endoscope 10, first video processor 20, and first light source 30 are technologically improved to produce the second endoscope 40, second video processor 50, and the second light source 60. In the light of an endoscope apparatus including the first endoscope 10, first video processor 20, and the first light source 30, an endoscope apparatus including the second endoscope 40, second video processor 50, and second light source 60 is provided as a next-generation endoscope apparatus.

In the endoscope system of this embodiment, the CCD 18 in the first endoscope 10 is of a different type from the CCD 48 in the second endoscope 40. This results in a difference in the number of pixels of a CCD or in the driving mode deriving from the differences in the number of drive signals for driving a CCD, drive voltage, drive signal phase, and drive signal waveform. Therefore, the first endoscope 10 is compatible only with the first video processor 20, and the second endoscope 40, with the second video processor 50. Thus, the endoscopes and video processors are employed in pairs.

Strictly speaking, the drive condition for driving a certain type of CCD optimally is not restricted to a specific value. The CCD can be driven at, for example, 60 fields per second or 30 fields per second. This invention provides compatibility between a CCD and a video processor (signal processor). That is to say, when a certain video processor can drive two types of CCDs optimally, these two types of CCDs are defined as of the same type. When only one of the two CCDs is driven optimally, the CCDs are defined as of different types.

Figure 2:
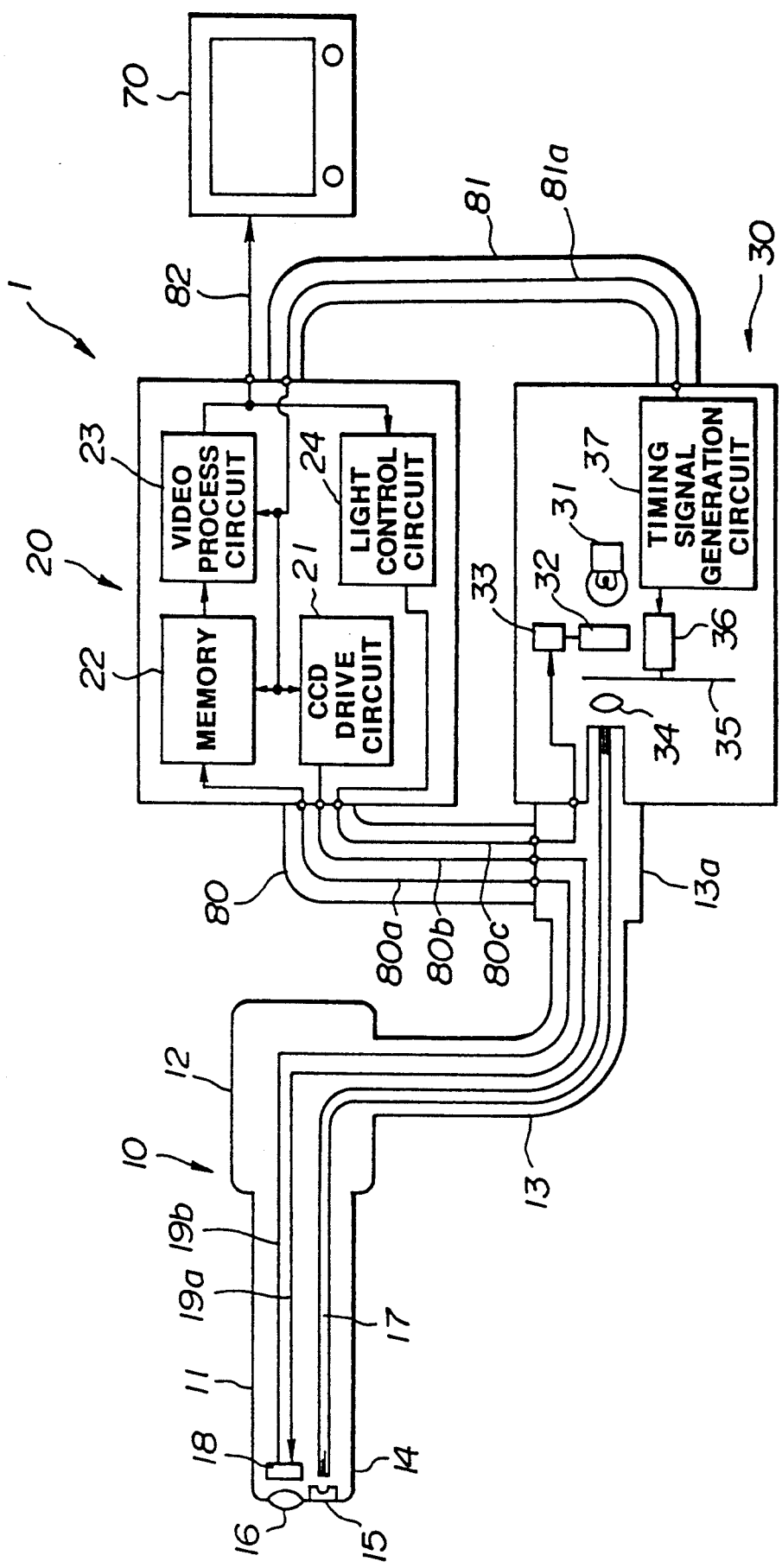
Figure 3:
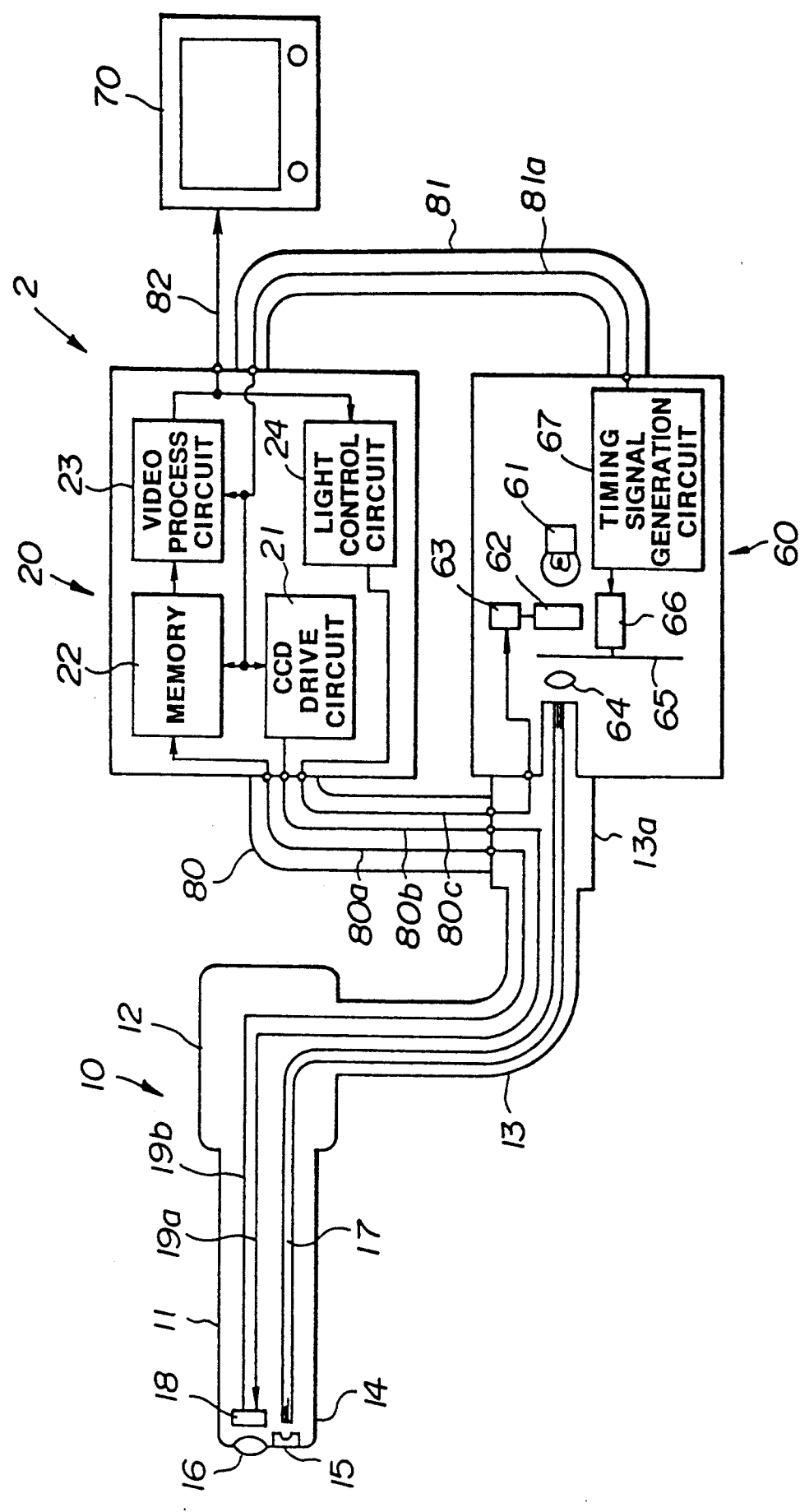
Figure 4:
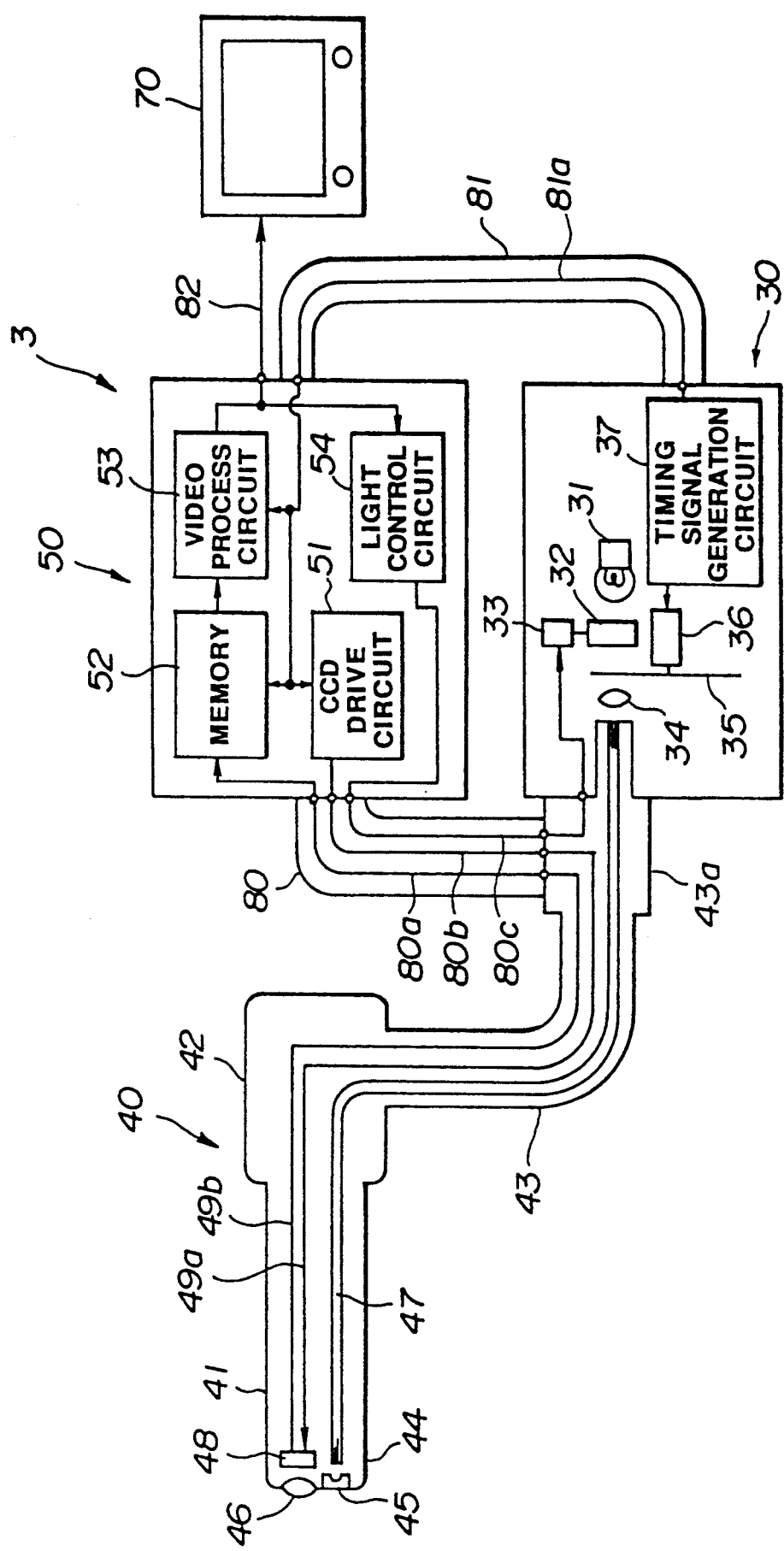
Figure 5:
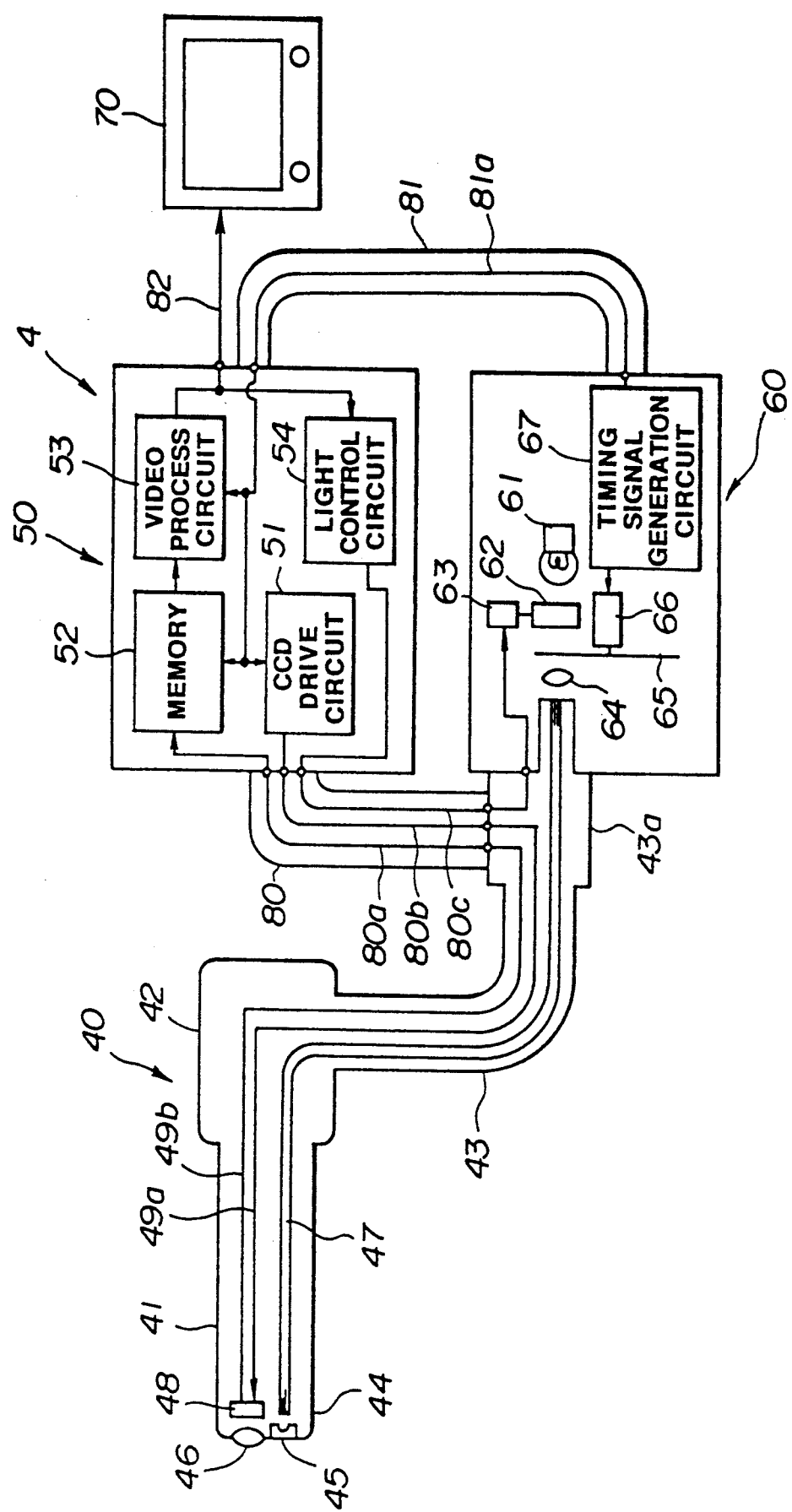

If a user who owns the endoscope apparatus 1 shown in FIG. 2 including the first endoscope 10, first video processor 20, and first light source 30 wants to improve the performance of some facility, the first and second light sources 30 and 60 may be used in combination to form endoscope apparatuses 2, 3, and 4 as shown in FIGS. 3 to 5 according to his/her needs.

That is, this endoscope system allows users to upgrade part of the functions without purchasing a whole new endoscope apparatus. In addition, a higher-grade apparatus need not be installed to support multiple endoscopes. Thus, enormous equipment investment is not required and only minimum equipment investment is needed to implement state-of-the-art technologies only in the facilities to be upgraded.

First, and endoscope apparatus i shown in FIG. 2 will be described. The endoscope apparatus 1 is formed by connecting a first endoscope 10 to a first light source 30, and the first light source 30 to a first video processor 20 using a first connection cable 80 and a second connection cable 81 which can be disconnected freely. Then, the first video processor 20 is connected to a TV monitor 70 via a video signal cable 82 that can be disconnected freely.

The first endoscope 10 comprises an elongated insertion tube 11 which can be inserted into a subject, a large-diameter operation unit 12 coupled to the back of the insertion tube and a universal cord 13 extending from the side of the operation unit 12. The first endoscope 10 and the first light source 30 are connected using a connector 13a installed at the back of the universal cord 13, although the first endoscope 10 and the first light source 30 can be disconnected freely. Thus, the first endoscope 10 and first light source 30 are coupled optically.

A rigid distal end 14 is formed at the tip of the insertion tube The distal end 14 is provided with an illumination optical system 15 made up of an illumination lens for emitting illumination light outward and an observation optical system 16 made up of an objective lens for forming an optical image of a subject.

The illumination optical system 15 is facing the emission end of a light guide 17 formed with a fiber bundle. The light guide 17 runs through the insertion tube 11, operation unit 12, and universal cord 13. The incident end of the light guide 17 is arranged at the tip of the connector 13a, so that illumination light originating from the first light source 30 can travel through the illumination optical system 15 and illuminate a subject.

A CCD 18 for converting an optical image of a subject into an electric signal is built in at the image formation position of the observation optical system 16. Signal lines 19a and 19b for transmitting the drive and output signals of the CCD 18 run through the insertion tube 11, operation unit 12, and universal cord 13, then terminate on the side of the connector 13a.

On the other hand, the first video processor 20 comprises a CCD drive circuit 21 for driving the CCD 18, a memory 22 for storing the outputs of the CCD 18 for three frames associated with R, G, and B field sequential light components, a video process circuit 23 for reading data of one screen (three frames associated with R, G, and B field sequential light components) from the memory 22, converting the data into a video signal, then displaying the video signal on the TV monitor 70, and a light adjustment circuit 24 for generating a light adjustment signal for illumination light according to the output signal sent from the video process circuit 23, as well as a sample-and-hold circuit, a low-pass filter, and a matrix circuit, which are not shown.

The first light source 30 comprises an illumination lamp 31 for emitting white light, a luminance diaphragm 32 for controlling and varying the quantity of transmission light of the illumination lamp 31, a diaphragm drive motor 33 for driving the luminance diaphragm 32, a converging system 34 for converging light onto the incident end of the light guide of an endoscope connected, a rotary filter 34 which is located between the converging optical system 34 and luminance diaphragm 32, and includes R, G, and B color transmission filters arranged in the circumference of a disk-like frame, a rotary filter drive motor 36 for driving the rotary filter 35, and a timing signal generation circuit 37 for generating timing signals.

The first video processor 20 is connected to the first endoscope 10 and light source 30 via the first connection cable 80 extending from the side of the connector 13a of the universal cord 13, and to the first light source 30 via the second connection cable 81. Thus, the first endoscope 10, first video processor 20, and first light source 30 are coupled electrically.

The first connection cable 80 accommodates a signal line 80a for transmitting the output signals of the CCD 18, a signal line 80b for transmitting the drive signal sent from the CCD drive circuit 21, and a signal line 80c for transmitting the output signal of the light adjustment circuit 24. The second connection cable 81 accommodates a signal line 81a for transmitting the output signal of the timing generation circuit 37.

Specifically, the first video processor 20 mutually controls the first light source 30. The first video processor 20 is compatible with either the first or second light source 30 or 60. The first light source 30 or second light source 60 feeds a timing signal to each of the CCD drive circuit 21, memory 22, video process circuit 23, and light adjustment circuit 24. The timing signals control the operation of the endoscope system.

In the endoscope apparatus 1, the timing signal sent from the timing signal generation circuit 37 in the first light source 30 is fed to the rotary filter drive motor 36, as well as the CCD drive circuit 21, memory 22, and video process circuit 23 in the first video processor 20.

Then, the rotary filter 35 is rotated by the rotary filter drive motor 36 according to a specified timing. The CCD drive circuit 21 drives the CCD 18 in synchronization with the rotation of the rotary filter 35. The output signal is placed in the memory 22. Data stored in the memory 22 is read by the video process circuit 23 to generate an NTSC video signal. The NTSC video signal enters the light adjustment circuit 24.

The light adjustment circuit 24 generates a light adjustment signal for controlling the diaphragm drive motor 33 according to the output signal of the video process circuit 23. The light adjustment signal passes through the signal line 80c in the first connection cable 80, then goes to the diaphragm drive motor 33. Thus, the aperture of the luminance diaphragm 32 is controlled.

Light emitted from the illumination lamp 31 is optimized in luminance by the luminance diaphragm 32, transmitted to the rotary filter 35, then separated time-sequentially into light components having R, G, and B wavelengths. Then, the light components are converged onto the incident end of the light guide 17 by the converging optical system 34. Then, field sequential illumination light is routed by the light guide 17, then emitted over a wide angle from the illumination optical system 15.

As a result, an optical image of a subject illuminated is formed on the imaging plane of the CCD 18 by the observation optical system 16. The photoelectrically-transferred output of the CCD 18 is processed by the first video processor 20 to generate a video signal.

Then, an optimal observation image of the subject appears on the TV monitor 70.

In the foregoing first endoscope 10, the observation optical system 16 has an observation depth of, for example, 8 to 10 mm, and the CCD 18 is a monochrome CCD providing 1000000 pixels and a sensitivity of 150 mV. The first video processor 20 provides an S/N ratio of 40 dB for the brightness signal sent from the video process circuit 23. The illumination lamp 31 in the first light source 30 is a halogen lamp, or preferably, a xenon lamp providing a brightness of 4000000 Lux.

The timing signal generation circuit 37 in the first light source 30 generates a timing signal for rotating the rotary filter 29 at 20 rotations per second (20 frames per second) using the rotary filter drive motor 36. According to the timing signal, the CCD drive circuit 21 drives the CCD 18 at 60 frames per second.

When a user wants the endoscope apparatus 1 to provide higher light adjustment speeds, the user should purchase only a second light source 60. In this case, as shown in FIG. 3, the endoscope 10 is connected to the second light source 60, and the second light source 60, to the first video processor 20 via the first connection cable 80 and second connection cable 81. Then, the first video processor 20 is connected to the TV monitor 70 via the video signal cable 82. Thus, an endoscope apparatus 2 is formed.

The second light source 60, similarly to the first light source 30, comprises an illumination lamp 61 for emitting white light, a luminance diaphragm 62 for controlling and varying the quantity of transmission light from the illumination lamp 61, a diaphragm drive motor 63 for driving the luminance diaphragm 62, a converging optical system 64 for converging light on the incident end of a light guide of an endoscope connected, a rotary filter 65 which is installed between the converging optical system 64 and luminance diaphragm 62, and includes R, G, and B color transmission filters arranged in the circumference of a disk-like frame, a rotary filter drive motor 66 for rotating the rotary filter 65, and a timing signal generation circuit 67 for generating timing signals.

The second light source 60 provides higher performance than the first light source 30. This is to say, the illumination lamp 61 or a halogen lamp provides, for example, 6000000 Lux. The mass of the variable device of the luminance diaphragm 32 is reduced, and the power of the diaphragm drive motor 63 is increased. The timing signal generation circuit 37 generates timing signals at, for example, 30 frames per second (30 rotations per second), and the first video processor 20 drives the CCD 18 at 90 frames per second and outputs an NTSC video signal.

Therefore, a user who owns the first light source 30 can increase the luminance of illumination light from 4000000 Lux to 6000000 Lux), speed up light adjustment (lightened mass of the variable device in the luminance diaphragm 32 and higher powered diaphragm drive motor 63), and reduce color aberration (from 20 frames/sec to 30 frames/sec) merely by installing the second light source 60. Thus, the user can improve the system performance.

When a user of the first endoscope apparatus 1 is not annoyed with color aberration in endoscope images but wants to improve image resolution, the user has to install only the second endoscope 40 equipped with a CCD 48 providing more pixels than that in the first endoscope 10 and the second video processor 50 having an advanced imaging circuit technology. The first light source 30 can be used as it is.

Specifically, as shown in FIG. 4, the second endoscope 40 is connected to the first light source 30, then the first light source 30, to the second video processor 50 via the first connection cable 80 and second connection cable 81. Then, the second processor 50 is connected to the TV monitor 70 via the video signal cable 82. Thus, an endoscope apparatus 3 is formed.

The second endoscope 40, similarly to the first endoscope 10, comprises an elongated insertion tube 41 which can be inserted into a subject, a large-diameter operation unit 42 coupled to the back of the insertion tube 41, and a universal cord 43 extending from the side of the operation unit 42. The endoscope 40 can be freely disconnected from the first light source 30 by removing a connector 43a installed at the back of the universal cord 43.

A distal end 44 of the insertion tube 41 is provided with an illumination optical system 45 and an observation optical system 46. The illumination optical system 45 is facing the emission end of a light guide 47, and a CCD 48 is built in at the image forming position of the observation optical system 46.

The light guide 47 runs through the insertion tube 41, operation unit 42, and universal cord 43. The incident end of the light guide 47 is arranged at the tip of the connector 43a. The CCD 48 is connected to a signal line 49a for transmitting drive signals and a signal line 49b for transmitting output signals. The signal lines 49a and 49b run through the insertion tube 41, operation unit 42, and universal cord 43, and terminate on the side of the connector 43a.

The CCD 48 benefits from advanced semiconducting technology, and provides, for example, 200000 pixels and a sensitivity of 300 mV. With the upgraded sensitivity of the CCD 48, the f-number of an objective lens in the observation optical system 46 can be reduced. The observation depth ranges, for example, from 3 to 100 mm.

The second video processor 50 is designed exclusively for the CCD 48 which has a different number of pixels from the CCD 18 in the first endoscope 10. The second video processor has a configuration similar to that of the first video processor 20. Even when either the first light source 30 or second light source 60 is used in combination, the second video processor 50 drives the CCD 48 according to the timing signal, then processes the signal sent from the CCD 48 to generate a video signal properly.

Specifically, the second video processor 50 comprises a CCD drive circuit 51 for driving the CCD 48, a memory 52 for storing the outputs of the CCD 48 for three frames associated with R, G, and B field sequential light components, a video process circuit 53 for reading data of one screen (three frames associated with R, G, and B field sequential light components) from the memory 52, converting the data into an NTSC video signal, then displaying the NTSC video signal on the TV monitor 70, and a light adjustment circuit 54 for generating a light adjustment signal using the output signal of the video process circuit 53, as well as a sample-and-hold circuit, a low-pass filter, and matrix circuit, which are not shown.

The video process circuit 53 provides a higher S/N ratio of 45 dB for a brightness signal due to an advanced imaging circuit technology. A user who has used the first endoscope 10 and first video processor 20 can upgrade his/her system performance by installing the second endoscope 40 and second video processor 50. Specifically, the image resolution is increased (from 100000 pixels to 200000 pixels), the observation depth is reduced (from 8 to 100 mm to 3 to 100 mm), and the S/N ratio is increased (from 40 dB to 45 dB).

Thus, system performance can be upgraded with a minimum cost according to the needs from a user. Highest overall performance currently available can be realized by purchasing the second endoscope 40, second video processor 50, and second light source 60, and using an endoscope apparatus 4 shown in FIG. 5.

In the endoscope apparatus 4, the second endoscope 40 is connected to the second light source 60, the second light source 60, to the second video processor 50 via the first connection cable 80 and second connection cable 81, and the second video processor 50, to the TV monitor 70 via the video signal cable 82. Compared with the endoscope apparatus 1 made up of the first endoscope 10, first video processor 20, and first light source 30, the endoscope apparatus 4 can provide improved overall performance in terms of observation depth, resolution, quantity of illumination light, light adjustment speed, color aberration, and S/N ratio.

The second endoscope 40, second video processor 50, and second light source 60 may be designed to be more compact and lighter than the first endoscope 10, first video processor 20, and first light source 30. Not all of the functions of the second endoscope 40, second video processor 50, and second light source 60 have higher performance, but some of the functions may.

For example, in the second endoscope 40, the sensitivity of the CCD 48 may not necessarily be improved to reduce the observation depth of the observation optical system 46, and the number of fibers forming the light guide 47 may be reduced to lessen the diameter of the insertion tube 41. In the second video processor 50, the performance of the video process circuit 53 may be upgraded not to increase the S/N ratio but to raise the luminance of images. In the second light source 60, the increased quantity of light of the illumination lamp 61 may be used to increase luminance instead of the number of frames.

The first connection cable 80 and second connection cable 81 may be unique to each combination of the models of video processor and light source.

In this embodiment, the first video processor 20 and second video processor 50 are of the field sequential type. Therefore, the first light source 30 and second light source 60 are also of the field sequential type. All of the above-described equipment may instead be based on simultaneous imaging. The first video processor 20 may be of the simultaneous type, and the second video processor 50, of the field sequential, or vice versa. In any case, the first and second light sources 30 and 60 are used in common for simultaneous and field sequential imaging.

Figure 6:
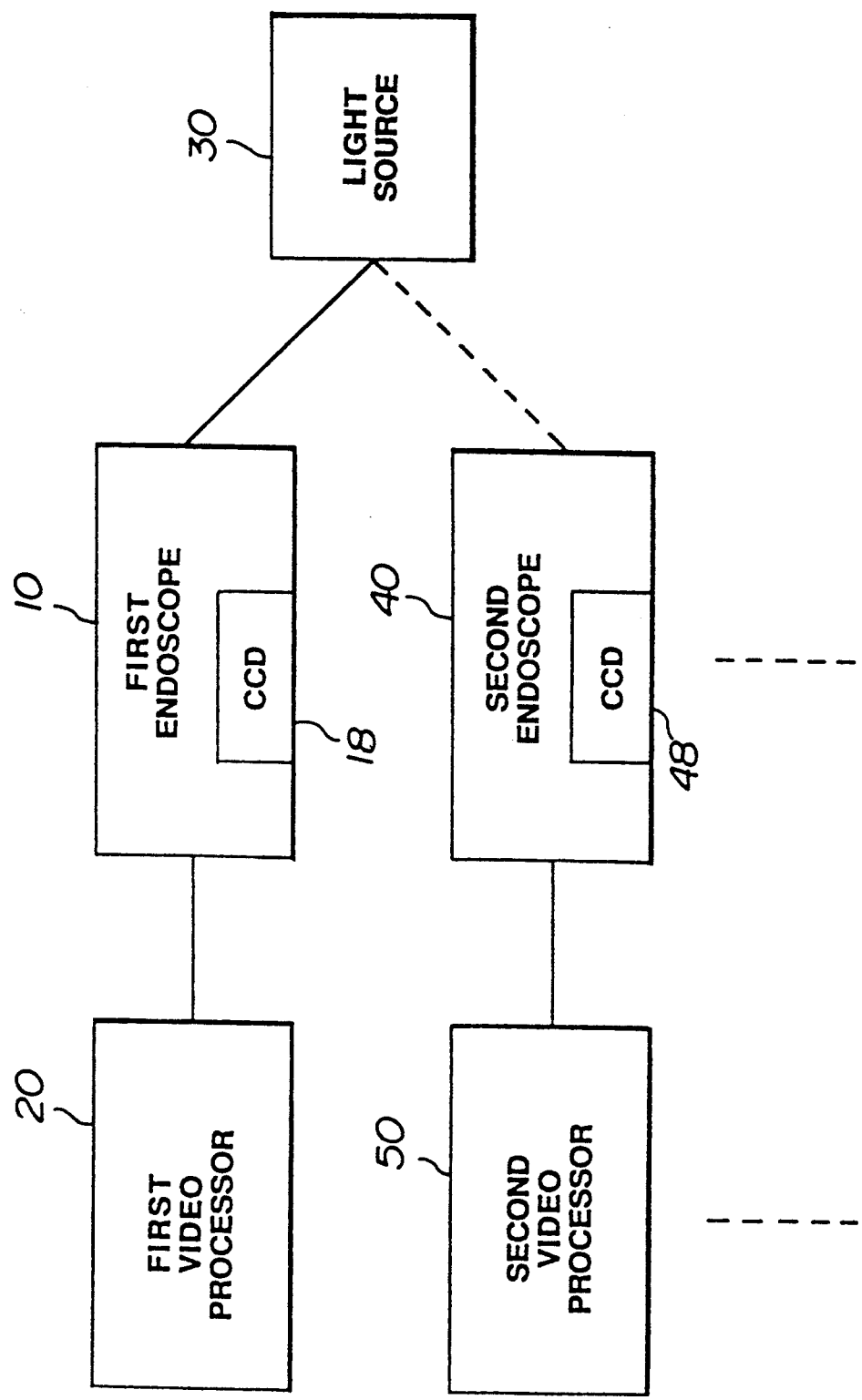
FIG. 6 is a schematic diagram showing the second embodiment of the present invention and the connecting relationships in the endoscope system.

FIG. 6 shows the second embodiment of the present invention.

The second embodiment is an example of an endoscope system in which a light source can be combined with any one of multiple sets of endoscopes and dedicated video processors.

Specifically, this embodiment can be described as a system configuration which is similar to that of the aforesaid endoscope system of the first embodiment but includes only a first light source 30. Even when the system configuration is expanded to include a first endoscope 10, a first video processor 20, a second endoscope 40, a second video processor 50, etc., a light source (first light source) 30 can be shared among the included equipment. The resolution of endoscopic images and the S/N ratio can be improved without installing a new light source.

The specific configuration and functions shall be represented by the endoscope apparatus 1 of the first embodiment shown in FIG. 2 and the endoscope apparatus 3 shown in FIG. 4.

Herein, both the first video processor 20 and second video processor 50 are preferably of either the field sequential or simultaneous type. This is because when both video processors are of the same type, the light source 30 may be dedicated to field sequential or simultaneous imaging. This reduces the cost and size of the light source 30.

Even when the light source 30 can be used in common for field sequential and simultaneous imaging, it is preferred that the first and second video processors 20 and 50 are of the same type. This is because the field sequential and simultaneous imaging modes have unique advantages and disadvantages. For example, when the field sequential mode is switched to the simultaneous mode, users may not always be satisfied with the resultant images because of unexpected disadvantages of simultaneous imaging. On the contrary, when the field sequential mode is exchanged for a technologically-improved field sequential mode, it will not dissatisfy any user. This is also true for transition from a current simultaneous mode to an improved simultaneous mode.

Figure 7:
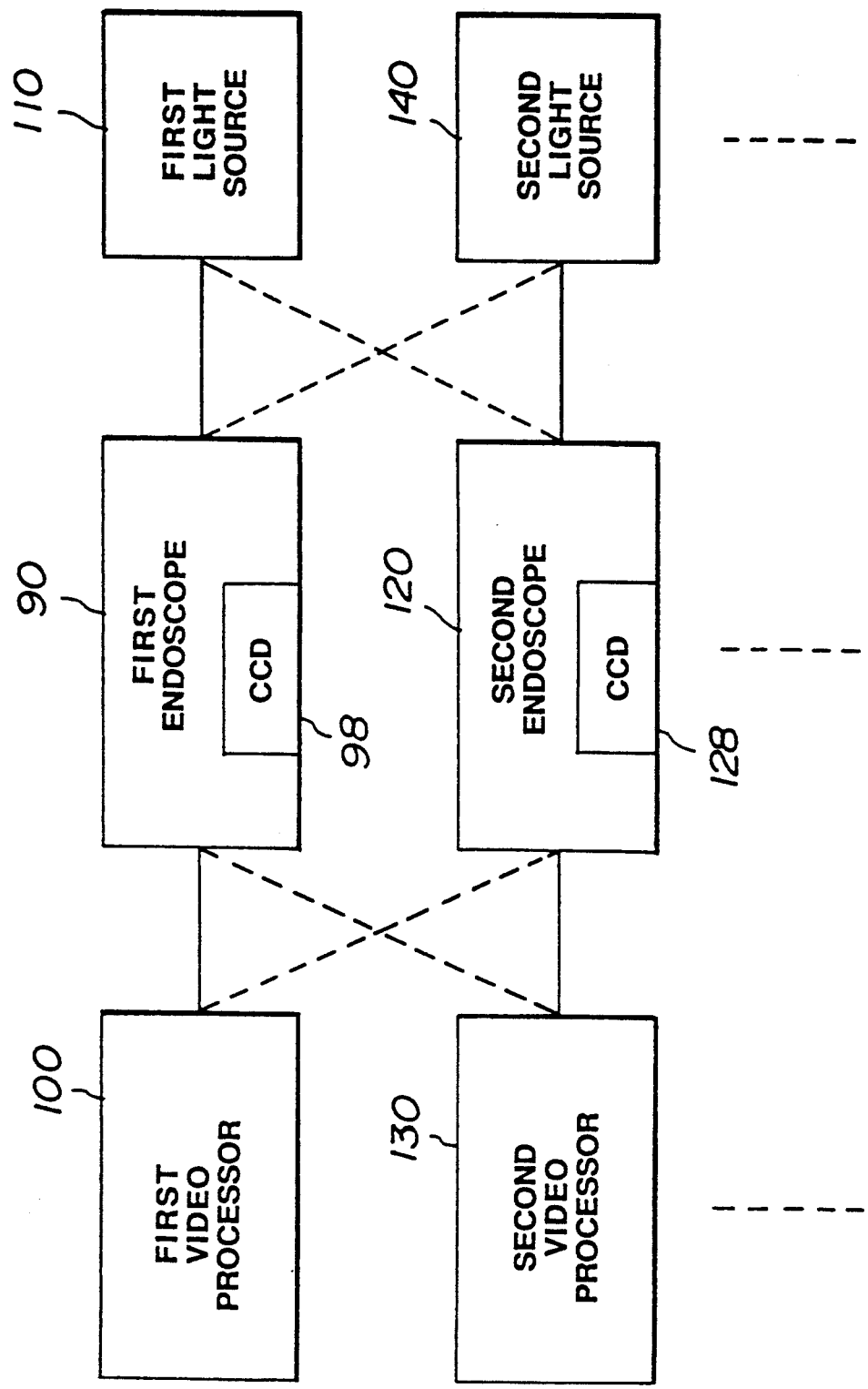
FIGS. 7 to 9 show the third embodiment of the present invention.
Figure 8:
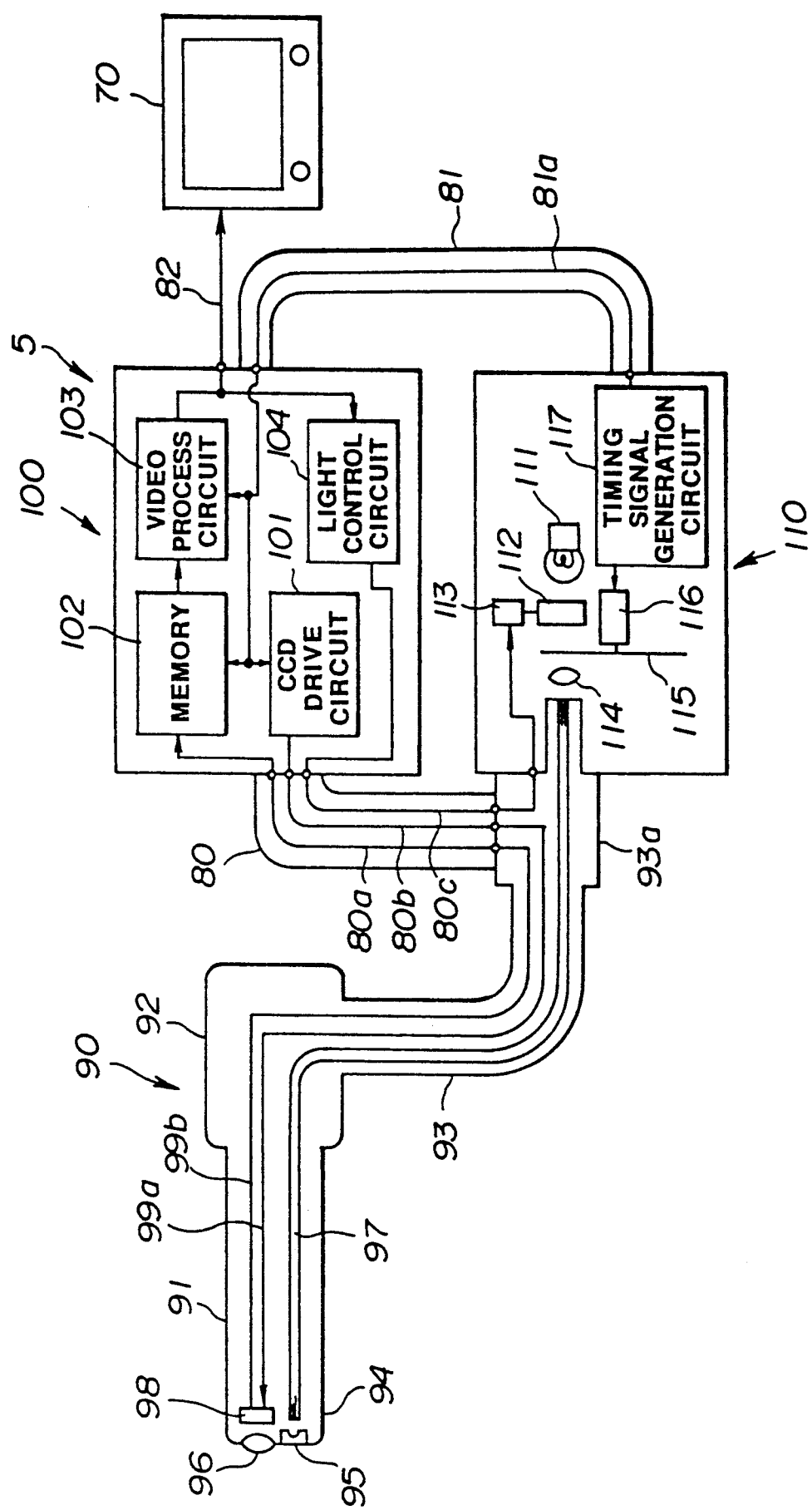
Figure 9:
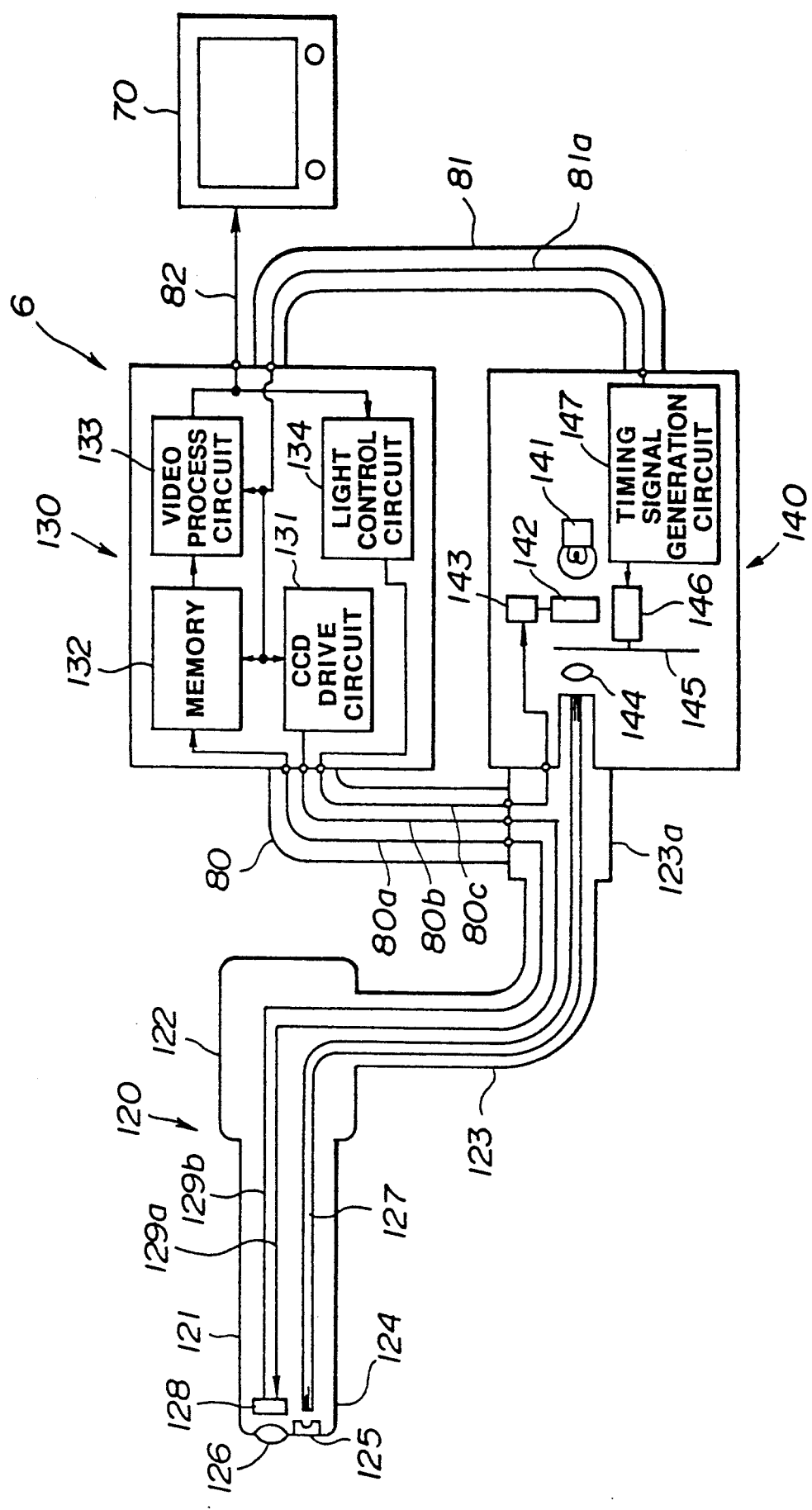

FIGS. 7 to 9 show the third embodiment of the present invention.

According to the third embodiment, an endoscope system having multiple endoscopes, multiple video processors, and multiple light sources, includes at least one endoscope equipped with a CCD compatible with at least two video processors. As shown in FIG. 7, any one of multiple light sources can be used in combination with a pair of an endoscope and video processor.

Specifically, as shown in FIG. 7, an endoscope system of this embodiment comprises a first endoscope 90 equipped with a CCD 98, a first video processor 100, a first light source 110, a second endoscope 120 equipped with a CCD 128, a second video processor 130, and a second light source 140. First, as shown in FIG. 8, the first endoscope 90 is connected to the first light source 110, and the first light source 110, to the first video processor 100 via a first connection cable 80 and a second connection cable 81. The first video processor 100 is connected to a TV monitor 70 via a video signal cable 82. Thus, an endoscope apparatus 5 is formed.

The first endoscope 90, similarly to that in the aforesaid first embodiment, comprises an elongated insertion tube 91 which can be inserted into a subject, a large-diameter operation unit 92 coupled to the back of the insertion tube 91, and a universal cord 93 extending from the side of the operation unit 92. The first endoscope 90 can be freely disconnected from the first light source 100 by removing a connector 93a installed at the back of the universal cord 93.

A distal end 94 of the insertion tube 91 is provided with an illumination optical system 95 and an observation optical system 96. The illumination optical system 95 is facing the emission end of a light guide 97. A CCD 93 is built in at the image forming position of the observation optical system 96.

The light guide 97 accommodates the insertion tube 91, operation unit 92, and universal cord 93. The incident end of the light guide 97 is arranged at the tip of the connector 93a. A CCD 98 for converting an optical image of a subject into an electric signal is built in at the image forming position of the observation optical system 96. Signal lines 99a and 99b for transmitting drive and output signals of the CCD 98 are routed through the insertion tube 91, operation unit 92, and universal cord 93, arranged at the side of the connector 93a, then connected to the first video processor 100 via the first connection cable 80.

The first video processor 100, similarly to that in the aforesaid first embodiment, is connected to the first endoscope 90 and first light source 110 via the first connection cable 80 extending from the side of the connector 93a, and to the first light source 110 via the second connection cable 81. Similarly to the video processors 20 and 50 in the aforesaid first embodiment, the first video processor 100 comprises a CCD drive circuit 101, a memory 102 for storing the outputs of the CCD 93 for three frames associated with R, G, and B field sequential light components, a video process circuit 103 for reading data of one screen (three frames associated with R, G, and B field sequential light components) from the memory 102, converting the data into an NTSC video signal, then displaying the NTSC video signal on the TV monitor 70, and a light adjustment circuit 104 for generating a light adjustment signal for illumination light according to the output signal of the video process circuit 103.

The first light source 110 has the same configuration as that in the aforesaid first embodiment, comprising an illumination lamp 111, a luminance diaphragm 112, diaphragm drive motor 113, a converging optical system 114 for converging light on the incident end of the light guide of an endoscope connected, and R, G, and B rotary filter 115 installed between the converging optical system 114 and luminance diaphragm 112, a rotary filter drive motor 116, and a timing signal generation circuit 117.

The first video processor 100 is compatible with either first or second light source 110 or 140. The first light source 110 or second light source 140 feeds a timing signal to each of the CCD drive circuit 101, memory 102, video process circuit 103, and light adjustment circuit 104. The operations of the endoscope apparatus based on the timing signals are identical to those in the aforesaid first embodiment.

Next, an endoscope apparatus 6 shown in FIG. 9 will be described. The endoscope apparatus 6 has the same connecting relationships as the endoscope apparatus 5. A second endoscope 120 is connected to a second light source 140, and the second light source 140, to a second video processor 130 via a first connection cable 80 and a second connection cable 81. Then, the second video processor 130 is connected to a TV monitor 70 via a video signal cable 82.

The second endoscope 120 comprises an elongated insertion tube 121 which can be inserted into a subject, a large-diameter operation unit 122 coupled to the back of the insertion tube 121, and a universal cord 123 extending from the side of the operation unit 122. The second endoscope 120 can be freely disconnected from the second light source 140 by removing a connector 123a installed at the back of the universal cord 123.

The universal cord 123 accommodates a light guide 127 whose emission end is facing an illumination optical system 125 installed at a distal end 124 of the insertion tube 121, and incident end is arranged at the tip of the connector 123a.

The signal lines 129a and 129b for transmitting drive and output signals of the CCD 128 which is installed at the image forming position of the observation optical system 126 located at the distal end 124 pass through the insertion tube 121, operation unit 122, and universal cord 123 to reach the side of the connector 123a.

The second video processor 130, similarly to the first video processor 100, comprises a CCD drive circuit 131, a memory 132 for storing the outputs of the CCD 128 for three frames associated with R, G, and B field sequential light components, a video process circuit 133 for reading data of one screen (three frames associated with R, G, and B field sequential light components) from the memory 132, converting the data into an NTSC video signal, then displaying the NTSC video signal on the TV monitor 70, and a light adjustment circuit 134 for generating a light adjustment signal for illumination light according to the output signal of the video process circuit 133. The second video processor 130 is connected to the second endoscope 120 and second light source 140 via the first connection cord 80 extending from the side of the connector 123a, and to the second light source 140 via the second connection cable 81.

The second video processor 130 is compatible with the first and second light sources 110 and 140. The first light source 110 or second light source 140 feeds a timing signal to each of the CCD drive circuit 131, memory 132, and video processing circuit 133, thus controlling the operations of the endoscope apparatus.

The second light source 140 has the same configuration as the first light source 110, comprising an illumination lamp 141, a luminance diaphragm 142, a diaphragm drive motor 143, a converging optical system 144 for converging light on the incident end of the light guide of an endoscope connected, and R, G, and B rotary filter 145 installed between the converging optical system 144 and luminance diaphragm 142, a rotary filter drive motor 146, and a timing signal generation circuit 147.

The second endoscope 120, second video processor 130, and second light source 140 forming the endoscope apparatus 6 are improved versions of the first endoscope 90, first video processor 100, and first light source 110 forming the endoscope apparatus 5.

Specifically, the second endoscope 120 weighs less than the first endoscope 90 as a whole. Besides, the durability against disinfection or sterilization is improved so that autoclave can be done. The insertion tube 121 of the second endoscope 120 has a smaller external diameter, permitting superb resiliency and flexibility. The light guide 127 provides higher permeability, resulting in improved light transmission efficiency. The CCD 128 has the same chip as the CCD 93 of the first endoscope 90, which, however, is packaged more compactly.

The CCD drive circuit 131 and memory 132 incorporated in the second video processor 130 ar identical to those in the first video processor 100. However, the second video processor 130 is more compact as a whole. The video process circuit 133 and light adjustment circuit 134 incorporated in the second video processor 130 have higher performance.

That is to say, in the video process circuit 133, the S/N ratio is increased, the color reproducibility is improved due to installation of a color operation matrix circuit, and an electronic zoom function is installed. The light adjustment circuit 134 is improved so that it can adjust light properly even when the distal end of an endoscope is oriented in the longitudinal axial direction of an organ or facing the wall of an organ.

The second light source 140 is designed more compactly as a whole than the first light source 110, which provides higher luminance because of the increased quantity of light of the illumination lamp 141, the upgraded mechanism of the diaphragm drive motor 143, the improved color balance of the rotary filter 145, and the larger aperture.

In this case, the CCD 98 in the first endoscope 90 is of the same type as the CCD 128 in the second endoscope 120, which is compatible with the first video processor 100 and second video processor 130. The first light source 110 and second light source 140 can be used in combination with either the first endoscope 90 or second endoscope 120, and either the first video processor 100 or second video processor 130.

Therefore, users merely have to install necessary equipment according to their needs and form an endoscope apparatus as shown in FIG. 7. Users will not incur an enormous load but can implement the results of latest technological improvements in equipment whose performance they want to improve.

Other combinations of the first endoscope 90, first video processor 100, first light source 110, second endoscope 120, second video processor 130, and second light source 140 are subject to those for the endoscope apparatuses 5 and 6. The description will, therefore, be omitted.

The CCD 98 in the first endoscope 90 is not necessarily of the same type as the CCD 128 in the second endoscope 120. In this case, despite a slightly limited number of combinations of an endoscope and a video processor, the advantages of the present invention deriving from system expendability will be exploited satisfactorily.

For example, the CCD 98 in the first endoscope 90 may be compatible both with the first and second video processors 100 and 130, while the CCD 128 in the second endoscope 120 may be compatible only with the second video processor 130.

In this case, a user who owns first endoscope 90 and first video processor 100 can improve video processing performance merely by purchasing the second video processor 130. If the user purchases the second endoscope 120 in the following fiscal year, he/she will be able to improve endoscopic performance. Thus, an endoscope system can be upgraded gradually within a limited annual budget.

The CCD 98 in the first endoscope 90 may be compatible only with the first video processor 100, while the CCD 128 in the second endoscope 120 may be compatible both with the first and second video processors 100 and 130. For this endoscope system, for example, the second endoscope 120 is purchased in the initial fiscal year, and the second video processor 130, in the following fiscal year. Thus, the endoscope system can be upgraded year after year within a limited annual budget.

Figure 10:
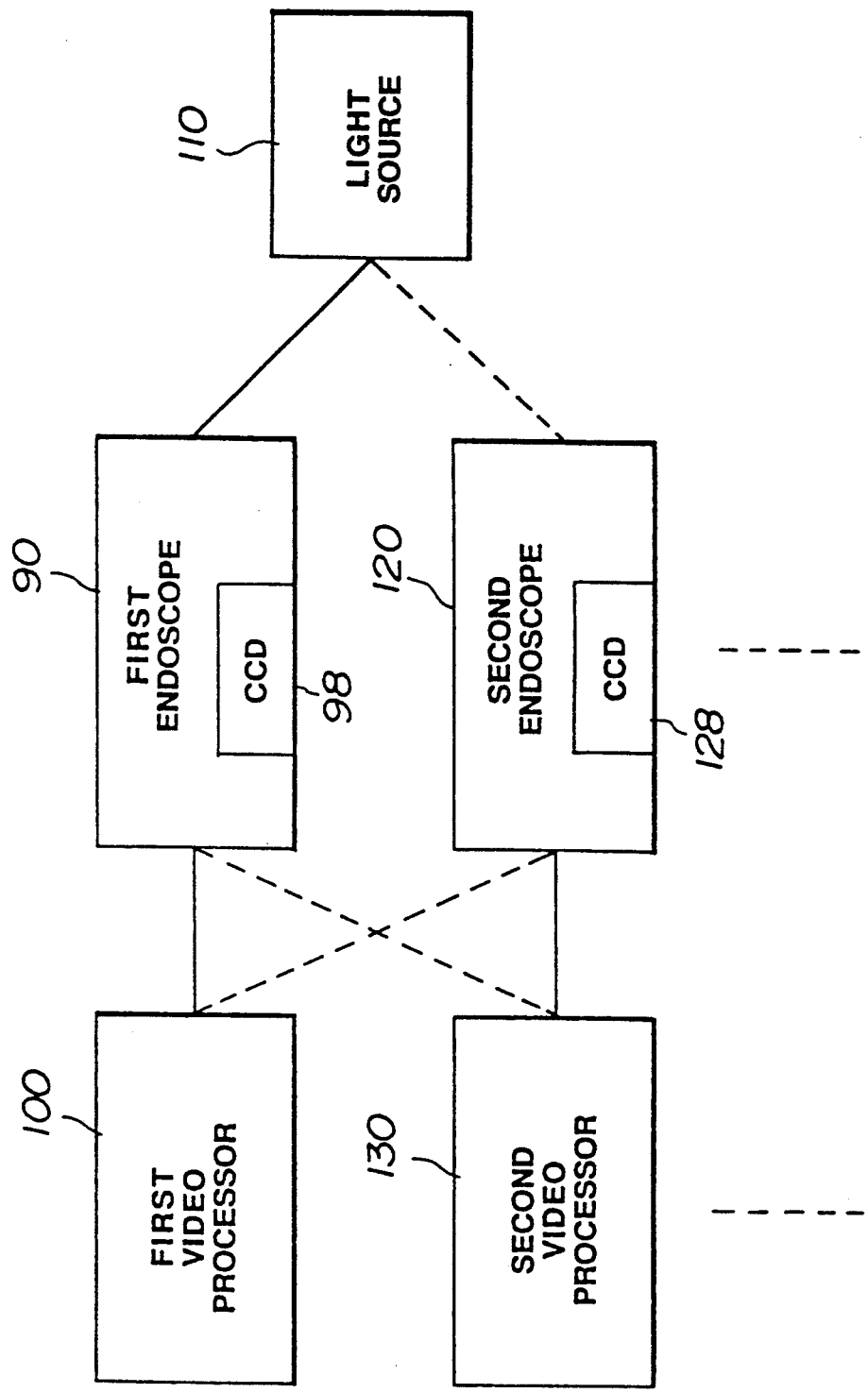
FIG. 10 is a schematic diagram showing the fourth embodiment of the present invention and the connecting relationships in an endoscope system.

FIG. 10 shows the fourth embodiment of the present invention.

The fourth embodiment has a system configuration which is similar to that of the endoscope system of the third embodiment but includes only a first light source 110. Even when the system configuration is expanded to include a first endoscope 90, a first video processor 100, a second endoscope 120, a second video processor 130, etc., a light source (first light source) 110 can be shared among the included equipment. A new light source need not be installed. Nevertheless, the endoscopic image resolution and S/N ratio can be improved.

The specific configuration and functions are identical to those of the third embodiment, which shall be represented by the endoscope apparatus 5 shown in FIG. 8.

Figure 11:
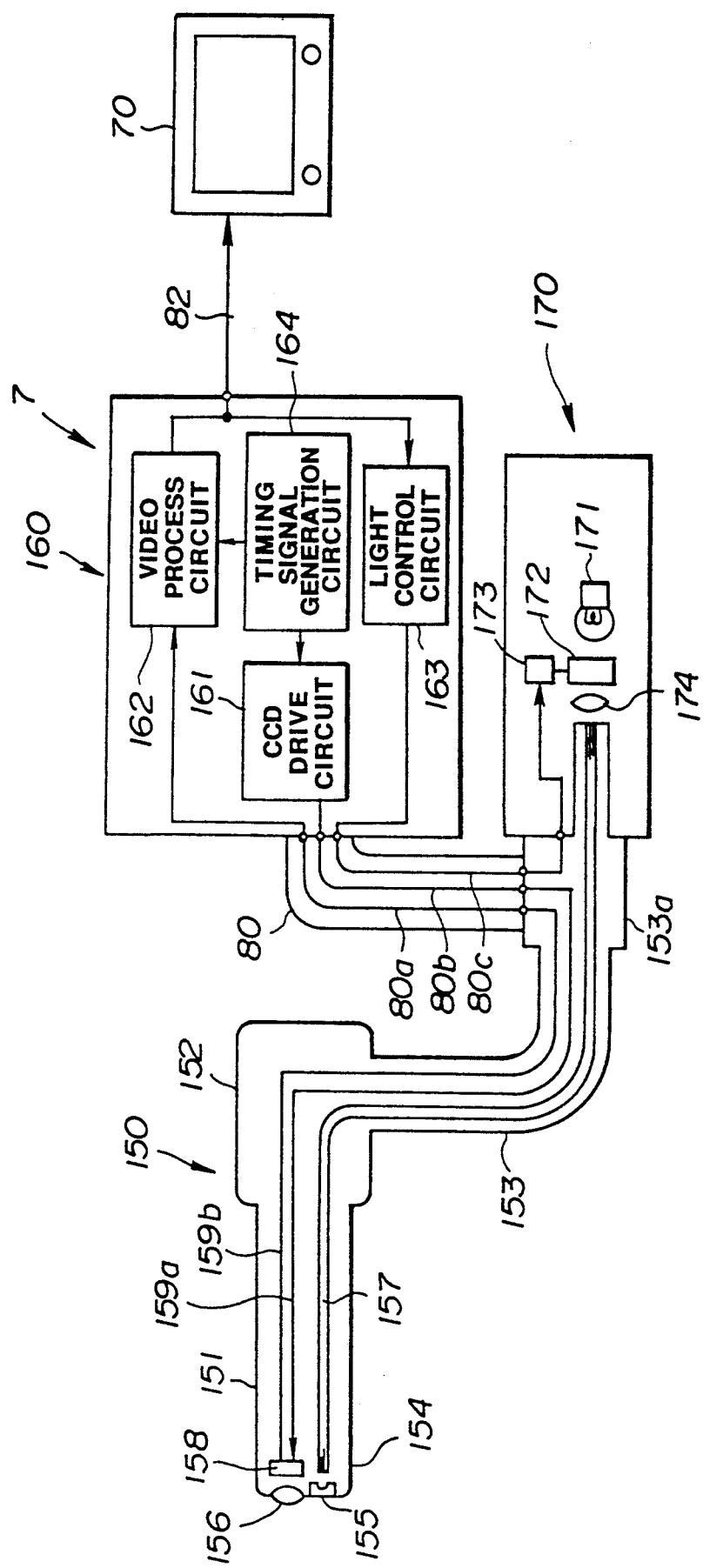
FIGS. 11 and 12 show the fifth embodiment of the present invention.
Figure 12:
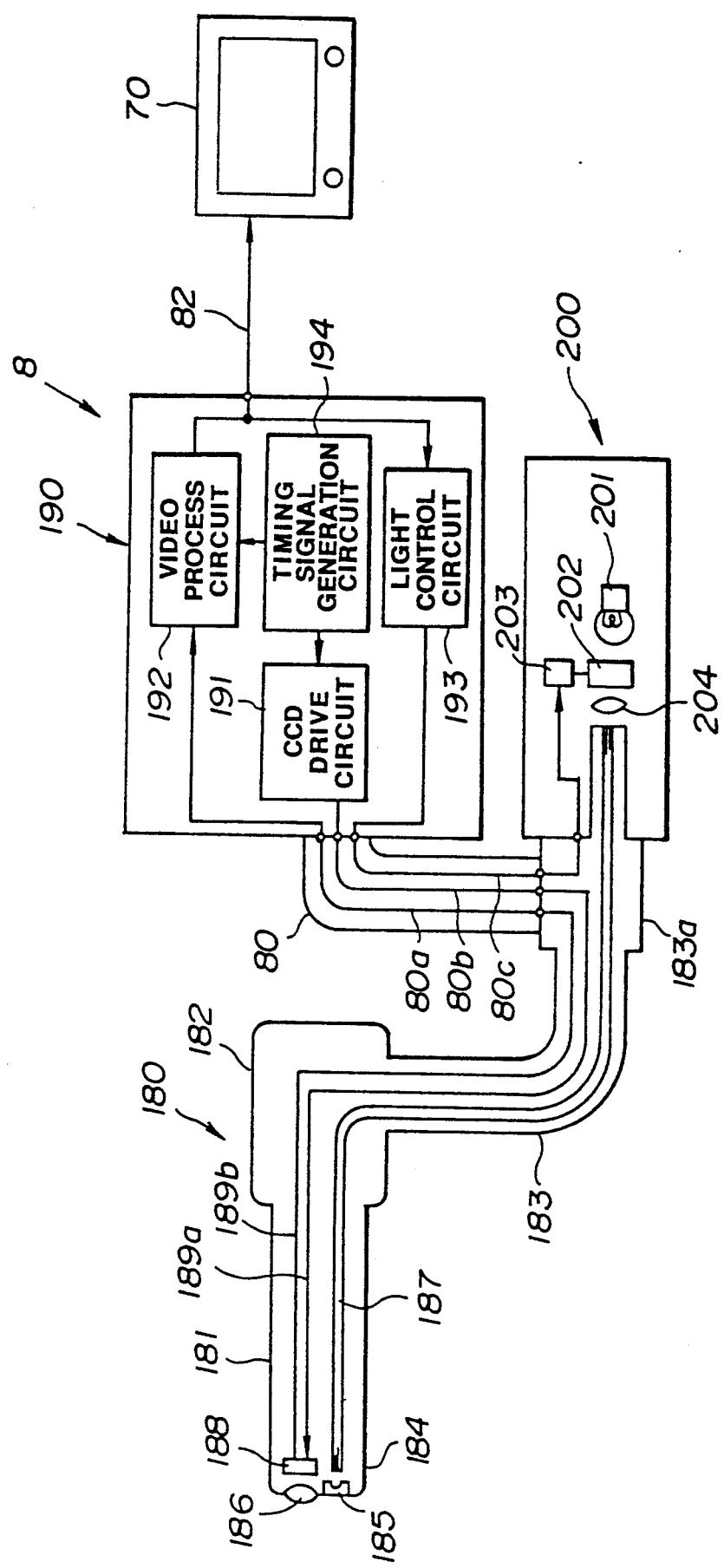

FIGS. 11 and 12 show the firth embodiment of the present invention.

The aforesaid embodiments are endoscope systems made up of field sequential type equipment, while this embodiment is an endoscope system made up of simultaneous type equipment.

This endoscope system includes a first endoscope 150, a first video processor 160, a first light source 170, a second endoscope 180, a second video processor 190, and a second light source 200, as shown in FIGS. 11 and 12.

In an endoscope apparatus 7 shown in FIG. 11, the first endoscope 150 is connected to the first light source 170, and the first light source 170, to the first video processor 160 via a first connection cable 80 described in the aforesaid first embodiment. The first video processor 160 is connected to a TV monitor 70 via a video signal cable 82. An endoscope apparatus 8 shown in FIG. 12 is formed by connecting the second endoscope 180 to the second light source 200, the second light source 200 to the second video processor 190 via the first connection cable 80, and the second video processor 160, to a TV monitor 70 via the video signal cable 82.

The first endoscope 150 comprises an elongated insertion tube 151 which can be inserted into a subject, a large-diameter operation unit 152 coupled to the back of the insertion tube 151, and a universal cord 153 extending from the side of the operation unit 152. The first endoscope 150 can be freely disconnected from the first light source 170 by removing a connector 153a installed at the back of the universal cord 153.

A rigid distal end 154 is formed at the tip of the insertion tube 151, and provided with an illumination optical system 155 and an observation optical system 156. The illumination optical system 155 is facing the emission end of a light guide 157. The light guide 157 runs through the insertion tube 151, operation unit 152, and universal cord 153. The incident end of the light guide 157 is arranged at the tip of the connector 153a.

A CCD 158 with a color mosaic filter on its imaging plane is built in at the image forming position of the observation optical system 156. Signal lines 159a and 159b for transmitting drive and output signals of the CCD 158 runs through the insertion tube 151, operation unit 152, and universal cord 153, and terminates on the side of the connector 153a.

The first video processor 160 comprises a CCD drive circuit 161 for driving a CCD, a video process circuit 162 for converting the signal sent from the CCD into an NTSC video signal, and displaying the NTSC video signal on the TV monitor 70, a light adjustment circuit 163 for generating a light adjustment signal using the output signal of the video process circuit 162, and a timing signal generation circuit 164 for generating a timing signal for determining a CCD drive timing or a timing of reading a signal from the CCD, and feeding the timing signal to each of the CCD drive circuit 161 and video process circuit 162.

The first light source 170 comprises an illumination lamp 171 for emitting white light, a luminance diaphragm 172 for controlling and varying the quantity of transmission light originating from the illumination lamp 171, a diaphragm drive motor 173 for driving the luminance diaphragm 172, and a converging optical system 174 for converging light onto the incident end of the light guide of an endoscope connected.

The first video processor 160 and first endoscope 150 are electrically coupled via the first connection cable 80 extending from the side of the connector 153a of the universal cord 153. The drive signal sent from the CCD drive circuit 161 passes through the signal line 80b of the first connection cable 80, then enters the CCD 158. The output signal sent from the CCD 158 passes through the signal line 80a of the first connection cable 80, then enters the video process circuit 162.

The first video processor 160 is electrically coupled with the first light source 170 via the first connection cable 80. The signal line 80c of the first connection cable 80 is used merely for transmitting the light adjustment signal sent from the light adjustment circuit 163 to the diaphragm drive motor 173 of the first light source 170. The first video processor 160 controls the first light source 170.

In this case, the first light source 170 is compatible with either the first endoscope 150 or second endoscope 180, and either the first video processor 160 or second video processor 190. The first light source 170 supplies properly adjusted light to an endoscope connected over a light adjustment signal. This is also true for the second light source 200.

On the other hand, in an endoscope apparatus 8 shown in FIG. 12, the second endoscope 180 includes an elongated insertion tube 181 which can be inserted into a subject, a large-diameter operation unit 182 coupled to the back of the insertion tube 181, and a universal cord 183 extending from the side of the operation unit 182. The second endoscope 180 can be freely disconnected from the second light source 200 by removing a connector 183a installed at the back of the universal cord 183.

The universal cord 183 accommodates a light guide 187 whose emission end is facing an illumination optical system 185 installed at a distal end 184 of the insertion tube 181 and incident end is arranged at the tip of the connector 183a.

The universal cord 183 accommodates signal lines 189a and 189b for transmitting drive and output signals of the CCD 188 which is installed at the image forming position of the observation optical system 186 located at the distal end 184 and provided with a color mosaic filter on its imaging plane. The signal lines 189a and 189b terminate on the side of the connector 183a.

The second endoscope 180 is more compact as a whole than the first endoscope 150, and more durable against disinfection or sterilization so that it can be autoclaved. The insertion tube 181 has a smaller external diameter, providing excellent resiliency and flexibility. The light guide 187 provides higher permeability, resulting in improved transmission efficiency. The CCD 188 employs an on-chip micro lens, providing improved sensitivity. If the CCD 188 chip is identical to the CCD 158 chip, the CCD 188 will also be compatible with the first video processor 160.

A second video processor 190 has the same configuration as the first video processor 160, comprising a CCD drive circuit 191, a video process circuit 192, a light adjustment circuit 193, and a timing signal generation circuit 194. A second light source 200 has the same configuration as the first light source 170, comprising an illumination lamp 201, a luminance diaphragm 202, a diaphragm drive motor 203, and a converging optical system 204.

In the second video processor 190, the CCD drive circuit 191 and timing signal generation circuit 194 are identical to those in the first video processor 160. The second video processor 190 is, however, more compact as a whole. The video process circuit 192 and light adjustment circuit 193 provide higher performance.

That is to say, the video process circuit 192 provides a higher S/N ratio, greater color reproducibility due to the modified color operation system, and more excellent contrast due to an improved gamma curve. The light adjustment circuit 193 is improved so that it can adjust light properly even when the distal end of an endoscope is oriented in the longitudinal axial direction of an organ or facing the wall of an organ.

The second light source 200 is designed more compactly as a whole than the first light source 170. The illumination lamp 201 provides a greater quantity of light, and the diaphragm drive motor 203, higher performance.

The combinations between the first endoscope 150 or second endoscope 180, the first video processor 160 or second video processor 190, and the first light source 170 or second light source 200 may vary depending on whether or not the CCD 158 and CCD 188 are of the same type. Specifically, endoscopes, video processors, and light sources are changed according to the connecting relationships of aforesaid embodiments shown in FIGS. 1, 6 and 10. When the first endoscope 150, first video processor 160, or first light source 170 is upgraded, users can install only the equipment required to improve system performance.

According to the present invention, it will be apparent that a variety of embodiments can be formed on a basis of the invention without department from the spirit and scope of the invention. This invention will be restricted to the appended claims but not limited to any specific embodiments.

What is claimed is:

1. An endoscope system, comprising:

a plurality of different endoscopes each of which has an illumination optical system for emitting light outward and an observation optical system for forming an optical image of a subject at a distal end of an insertion tube that can be inserted into said subject, and includes a different type of solid-state imaging device for converting the optical image of said subject formed by said observation optical system into an electric signal;

a plurality of different signal processors each of which is compatible with one of said plurality of different endoscopes according to the type of said solid-state imaging device, for driving said solid-state imaging device in simultaneous mode, and for processing the output signal of said solid-state imaging device to provide a video signal; and a light source which is compatible with any one of said plurality of different endoscopes for supplying light to said illumination optical system, wherein one of said plurality of different endoscopes is connected to a compatible one of said plurality of different signal processors and to said light source, thus forming an endoscope apparatus.

2. An endoscope system according to claim 1, wherein said endoscope converts the optical image of said subject into an electrical signal using said solid-state imaging device in simultaneous imaging mode, and said signal processor processes the signal sent from the solid-state imaging device in said endoscope in simultaneous imaging mode.

3. An endoscope system, comprising:

a plurality of different endoscopes each of which has an illumination optical system for emitting light outward and an observation optical system for forming an optical image of a subject at a distal end of an insertion tube that can be inserted into said subject, and includes a different type of solid-state imaging device for converting the optical image of said subject formed by said observation optical system into an electric signal;

a plurality of different signal processors each of which is compatible with one of said plurality of different endoscopes according to the type of said solid-state imaging device, for driving said solid-state imaging device in field sequential mode, and for processing the output signal of said solid-state imaging device to provide a video signal; and a light source which is compatible with any one of said plurality of different endoscopes for supplying light to said illumination optical system, wherein one of said plurality of different endoscopes is connected to a compatible one of said plurality of different signal processors and to said light source, thus forming an endoscope apparatus.

4. An endoscope system according to claim 1 or 3, wherein the solid-state imaging devices in said plurality of different endoscopes differ from one another in the number of pixels forming the imaging plane of said solid-state imaging device.

5. An endoscope system according to claim 1 or 3, wherein the solid-state imaging devices in said plurality of different endoscopes differ from one another in the driving mode for said solid-state imaging device.

6. An endoscope system according to claim 1 or 3, wherein the quantity of light of said light source is adjusted according to the signal said signal processor generates.

7. An endoscope system according to claim 1 or 3 wherein said light source supplies light to the illumination optical system of said endoscope, and said signal processor processes the signal sent from the solid-state imaging device in said endoscope.

8. An endoscope system according to claim 7 wherein a single timing signal generation circuit feeds a timing signal for supplying light to said light source, and a timing signal for driving the solid-state imaging device in said endoscope and processing the output signal sent from said solid-state imaging device to said signal processor.

* * * * *